(12) United States Patent
Kodama et al.

(10) Patent No.: US 8,071,153 B2
(45) Date of Patent: Dec. 6, 2011

(54) WHEY PROTEIN-CONTAINING GRANULES AND METHOD OF PRODUCING THE SAME

(75) Inventors: Takuya Kodama, Kawasaki (JP); Akio Tanaka, Fujimino (JP); Tetsuya Magarikaji, Kawasaki (JP)

(73) Assignee: Meiji Seika Kaisha, Ltd., Tokyo-to (JP)

( * ) Notice: Subject to any disclaimer, the term of this patent is extended or adjusted under 35 U.S.C. 154(b) by 492 days.

(21) Appl. No.: 12/226,354

(22) PCT Filed: Apr. 17, 2007

(86) PCT No.: PCT/JP2007/058329
§ 371 (c)(1),
(2), (4) Date: Oct. 16, 2008

(87) PCT Pub. No.: WO2007/123113
PCT Pub. Date: Nov. 1, 2007

(65) Prior Publication Data
US 2009/0098274 A1   Apr. 16, 2009

(30) Foreign Application Priority Data
Apr. 17, 2006 (JP) ................ 2006-113189

(51) Int. Cl.
*A23J 1/04* (2006.01)
(52) U.S. Cl. ........................................ 426/657
(58) Field of Classification Search ............ 426/657
See application file for complete search history.

(56) References Cited

U.S. PATENT DOCUMENTS
5,443,846 A * 8/1995 Yoshioka et al. ............ 424/498

FOREIGN PATENT DOCUMENTS

| | | |
|---|---|---|
| JP | 08-131083 | 5/1996 |
| JP | 09-313112 | 12/1997 |
| JP | 2001-516599 | 10/2001 |
| JP | 2003-189799 | 7/2003 |
| WO | 99/15024 | 4/1999 |
| WO | 2006/035979 | 4/2006 |

OTHER PUBLICATIONS

Nagasaka et al. JP 06113755 Derwent Abstract Only.*
Nagasaka et al. JP 06113755, Apr. 26, 1994—Derwent Abstract Only.*

* cited by examiner

*Primary Examiner* — D Lawrence Tarazano
*Assistant Examiner* — Elizabeth Gwartney
(74) *Attorney, Agent, or Firm* — Wenderoth, Lind & Ponack, LLP

(57) ABSTRACT

Disclosed are whey protein-containing granules which can dissolve a whey protein into water without forming insoluble lumps thereby making a solution containing the dissolved whey protein clear without turbidity, and a method for producing the same. The whey protein-containing granules are composed of a polyglycerin fatty acid ester having HLB of 13 to 18 and containing lauric acid as a constituent fatty acid. As the polyglycerin fatty acid ester, for example, monolauric acid decaglycerin ester or monolauric acid pentaglycerin ester may be used.

20 Claims, No Drawings

WHEY PROTEIN-CONTAINING GRANULES AND METHOD OF PRODUCING THE SAME

RELATED APPLICATION

The present application claims the priority of the Japanese Patent Application No. 2006-113189 filed on Apr. 17, 2006, and the specification of this Japanese application is incorporated herein by reference.

BACKGROUND OF THE INVENTION

1. Field of the Invention

The present invention relates to whey protein-containing granules and a method for producing the same.

2. Background Art

The whey protein is a protein contained in the milk serum (whey) obtained by removing casein and the like from milk, and comprises lactoalbumin, lactoglobulin, lactoferrin, and the like as main components. A whey protein is known to have such functions as a stamina improver, a fatigue reliever, an immunity enhancer, and the like, and in addition it is used as a protein supplement material in an athletic nutrient food, a diet food, and the like. The powders of this whey protein are highly hygroscopic, and when attempt is made to be dissolved in water as they are, the surface of powder clumps becomes a sort of candy to form lumps. Once they form lumps, the complete dissolution becomes difficult unless the lumps are broken with care and patience.

In order to make a hardly-soluble raw material soluble, making granules by binding the powders by granulation thereby facilitating penetration of water into them is generally practiced, and several attempts have been made to make whey protein-containing granules. For instance, the Japanese Patent Laid-Open Publication No. S63-22172 discloses a powdered or a granulated food composition composed of whey powders and the like and a surface active agent for foods in a liquid or a paste form. In this composition, a viscid surface active agent for foods is mixed with whey powders in order to improve handling properties of it, and the invention is nothing to do with the solubility of whey itself, thus the content of the surface active agent is high. Also, the Japanese Patent Laid-Open Publication Nos. H10-84868 and 2003-189799 discloses a milk substitute composition mainly containing whey and the like, characterized by containing lecithin and a polyoxyethylene glycerin fatty acid ester in it. This intends to suppress segregation of fat in the milk substitute and contains 10% by weight or more of fat, and thus does not have to do with dissolution of whey powders. In addition, as far as the present inventors know, when the compositions disclosed in these prior arts were dissolved in water, in any of these cases turbidity was observed, not resulting in transparency.

SUMMARY OF THE INVENTION

We have now found that solubility of whey protein-containing granules and transparency of the solution after their dissolution are remarkably improved by a specific polyglycerin fatty acid ester. The present invention is based on such a finding.

Accordingly, an object of the present invention is to provide the whey protein-containing granules having improved solubility and moreover transparency after their dissolution. In addition, the present invention aims to provide a method for producing the whey protein-containing granules.

According to one embodiment of the present invention, there is provided whey protein-containing granules comprising a polyglycerin fatty acid ester having HLB of 13 to 18 and containing lauric acid as its constituent fatty acid.

Furthermore, according to one embodiment in the present invention, there is provided a method for producing the whey protein-containing granules comprising a step of granulating a whey protein with a polyglycerin fatty acid ester having HLB of 13 to 18 and containing lauric acid as its constituent fatty acid, optionally together with a binder.

Furthermore, according to another embodiment in the present invention, there is provided a method for producing the whey protein-containing granules comprising steps of granulating a whey protein, optionally together with a binder, to obtain granules, and adding a polyglycerin fatty acid ester having HLB of 13 to 18 and containing lauric acid as its constituent fatty acid to the granules.

DETAILED DESCRIPTION OF THE INVENTION

A Polyglycerin Fatty Acid Ester

A polyglycerin fatty acid ester contained in the whey protein-containing granules according to the present invention is the one having HLB of 13 to 18 and containing lauric acid as its constituent fatty acid. In the present invention, the HLB value of a polyglycerin fatty acid ester is 13 to 18 and preferably 14 to 16. The HLB value within this range is preferable, since the granules do not easily form insoluble lumps and also an aqueous solution of high transparency may be obtained. The HLB is the numeric expression of the balance of relative strengths of hydrophilicity and lipophilicity of a surface active agent molecule, and the higher the HLB is, the higher the hydrophilicity becomes.

In the present invention, a molecule of a polyglycerin fatty acid ester contains one or more of the glycerin unit in it, and preferably 1 to 15 unit(s), and more preferably 5 to 10 units. As a result, there exist plural hydroxyl groups in the molecule, and therefore all of them may be esterified by lauric acid theoretically. Although its number may be determined within the range realizing the HLB values, the number of the ester by lauric acid is one according to the preferable embodiment of the present invention. In addition, although the position of the esterification may be determined appropriately within the range realizing the HLB values, it is preferable at the hydroxyl group near its terminal.

Since a polyglycerin fatty acid ester in the present invention may include a compound having one glycerin unit in the molecule, it may be referred to as simply "a glycerin fatty acid ester".

Thus, according to one preferable embodiment of the present invention, a polyglycerin fatty acid ester contained in the whey protein-containing granules of the present invention is preferably a compound represented by the following formula (I):

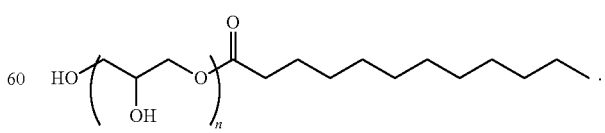

wherein the formula, n represents an integer of 1 to 15.

Further, according to another preferable embodiment of the present invention, a polyglycerin fatty acid ester contained in the whey protein-containing granules of the present invention is preferably monolauric acid decaglycerin ester or monolauric acid pentaglycerin ester.

In the present invention, the amount of the polyglycerin fatty acid ester to be added is not particularly restricted, but preferably about 0.5 to about 3% by weight relative to the whey protein-containing granules. By choosing the added amount within this range, formation of the insoluble lumps can be effectively prevented from occurring. On the other hand, when the added amount is too large, there may be a chance to affect the taste of a food and the like containing the whey protein-containing granules of the present invention. From this standpoint the upper limit may be determined.

The whey protein-containing granules according to the present invention have high transparency when dissolved in water. Specifically, the light transmittance of the solution, dissolving 5 parts by weight of the granules in 100 parts by weight of water, measured at the 800 nm wavelength is 80% or more, and, according to the preferred embodiments, 90% or more. The transmittance is obtained in the following way; 5 parts by weight of the whey protein-containing granules are dissolved in 100 parts by weight of water, and then the light transmittance is measured by irradiating an 800-nm wavelength light to the thus prepared solution in a cell having 10-mm width versus water as the comparative reference.

Further, when pH of the aqueous solution dissolving the whey protein-containing granules is near the isoelectric point of a whey protein (pH 4 to 5), precipitation occurs, and thus it is not preferable. Also considering the taste, pH of the aqueous solution dissolving the whey protein-containing granules is preferably 2.5 to 3.7, or more preferably 6 to 7.5. The pH measurement is done at the temperature of 25° C.

Whey Protein-Containing Granules and a Method for Producing Them

The whey protein-containing granules according to the present invention may be the whey protein-containing granules produced by a publicly known or a conventionally used method except that they contain the polyglycerin fatty acid esters. Accordingly, the whey protein-containing granules according to the present invention may be produced by a fluidized bed granulation, a tumbling granulation, an extrusion granulation, an agitation granulation, and the like. It is preferable to use a binder when granulating, and examples of the binder include an aqueous solution of such thickener polysaccharides as pullulan, gum arabic, guar gum, xanthan gum, locust bean gum, and the like.

Addition of the polyglycerin fatty acid ester to the granules may be carried out by mixing with powders of raw materials such as a whey protein and the like prior to the granulation, at the time of granulation, or after the granulation to the granules (for instance, it is sprayed as it is or as an aqueous solution to cover a part or all of the granules), and the like.

Thus, according to one preferable embodiment of the present invention, there is provided a method for producing the whey protein-containing granules comprising a step of granulating a whey protein with a polyglycerin fatty acid ester having HLB of 13 to 18 and containing lauric acid as its constituent fatty acid, optionally together with a binder.

Further, according to another preferable embodiment of the present invention, there is provide a method for producing the whey protein-containing granules granulating a whey protein, optionally together with a binder, and then adding a polyglycerin fatty acid ester having HLB of 13 to 18 and containing lauric acid as its constituent fatty acid to the obtained granules, wherein the addition is preferably carried out by spraying its aqueous solution. The embodiment of the addition of the polyglycerin fatty acid ester by the spraying is preferable as the whole granules may be covered by the polyglycerin fatty acid ester uniformly.

The amount of a whey protein in the whey protein-containing granules according to the present invention is not particularly limited, but it is preferably applied to the granules containing 30% by weight or more, and a high content of 60 to 95% by weight may also be allowed. The content of a whey protein in the present invention is calculated based on 100% by weight of the dry weight, which is obtained by subtracting water content from the weight of the granules as the final product.

The whey protein-containing granules according to the present invention may be used as they are or also as a composition containing a carrier material suitable for their uses. For example, they are used as a food or a drug.

Thus, according to one preferable embodiment of the present invention, a composition concurrently containing the whey protein-containing granules of the present invention and a carrier material is provided. In addition, according to another preferable embodiment of the present invention, a food or a drug comprising containing the whey protein-containing granules of the present invention is provided.

Further, the whey protein-containing granules according to the present invention may contain other components in accordance with their uses. For instance, they can contain a raw material contained in usual food granules, which include saccharides such as sucrose, glucose, maltose, fructose, lactose, trehalose, sorbitol, maltitol, xylitol, oligosaccharides, dextrin, soluble starch, and the like; acidulants such as citric acid, malic acid, tartaric acid, lactic acid, and the like; sweeteners such as stevia, aspartame, sucralose, acesulfame potassium, and the like; thickners such as pullulan, gum arabic, guar gum, xanthan gum, locust bean gum, and the like; minerals such as calcium, magnesium, potassium, iron, sodium, and the like; vitamins such as vitamins A, group B, C, D, E, K, and the like; amino acids such as valine, leucine, isoleucine, glutamine, lysine, methionine, and the like; fragrances such as a vanilla fragrance, a milk fragrance, a fruit fragrance, a drink fragrance, and the like.

EXAMPLES

The present invention will be explained more specifically by the following examples, but the present invention is not limited by these examples.

Test Examples

A batch comprising 75 parts by weight of a whey protein, 14.9 parts by weight of lactose, and 8.7 parts by weight of citric acid was granulated with mixing in a fluidized bed granulator at 65° C. and with spraying 10 parts by weight of a binder solution containing 5% by weight of pullulan and 1% by weight of sucralose dissolved in water. After completion of the spraying, they were dried at 85° C. until the water content reached 3% by weight, and then cooled to ordinary temperature to obtain the granules. Thus obtained granules were sprayed with 1.6 parts by weight of each of spray solutions composed of equal weights of an emulsifier shown in Table 1 and water (only water in Comparative Example 9) to obtain the whey protein-containing granules as the final products. A portion of 10 g of the whey protein-containing granules thus obtained was added into 200 g of water at 25° C. and evenly stirred by a spatula for 15 seconds to observe if the lumps were formed or not. Also, the light transmittance of the obtained solution at the wavelength of 800 nm was measured by using a spectrophotometer (UV-2400PC, manufactured by Shimadzu Corporation). Here, pH of each aqueous solution was 3.3. The results are shown in Table 1.

TABLE 1

|  | Kinds of emulsifiers | Formation of lumps | Transmittance |
|---|---|---|---|
| Example 1 | Sunsoft Q-12S | No | 97% |
| Example 2 | SunSoft A-121E | No | 95% |
| Comparative Example 1 | Sunsoft Q-17B | No | 34% |
| Comparative Example 2 | Sunsoft Q-17S | Yes | 79% |
| Comparative Example 3 | Sunsoft Q-175S | No | 56% |
| Comparative Example 4 | Sunsoft A-141E | Yes | 84% |
| Comparative Example 5 | Emasol L-10V | No | 40% |
| Comparative Example 6 | Poem J-0081HV | Yes | 89% |
| Comparative Example 7 | Ryoto Sugar Ester LWA-1570 | Yes | 96% |
| Comparative Example 8 | Ryoto Sugar Ester P-1670 | Yes | 90% |
| Comparative Example 9 | No emulsifier | Yes | 98% |

Sunsoft Q-12S monolauric acid decaglycerin ester (HLB 15.5), manufactured by Taiyo Kagaku Co., Ltd.
Sunsoft A-121E monolauric acid pentaglycerin ester (HLB 14.0), manufactured by Taiyo Kagaku Co., Ltd.
Sunsoft Q-17B mono-dioleic acid diglycerin ester (HLB 7.5), manufactured by Taiyo Kagaku Co., Ltd.
Sunsoft Q-17S monooleic acid decaglycerin ester (HLB 12.0), manufactured by Taiyo Kagaku Co., Ltd.
Sunsoft Q-175S pentaoleic acid decaglycerin ester (HLB 4.5), manufactured by Taiyo Kagaku Co., Ltd.
Sunsoft A-141E monomyristic acid pentaglycerin ester (HLB 13.0), manufactured by Taiyo Kagaku Co., Ltd.
Emasol L-10V monolauric acid sorbitan ester (HLB 8.6), manufactured by Kao Corporation
Poem J-0081HV monostearic acid decaglycerin ester (HLB 12.0), manufactured by Riken Vitamin Co., Ltd.
Ryoto Sugar Ester LWA-1570 lauric acid sugar ester (HLB 15.0), manufactured by Mitsubishi-Kagaku Foods Corporation
Ryoto Sugar Ester P-1670 palmitic acid sugar ester (HLB 16.0), manufactured by Mitsubishi-Kagaku Foods Corporation

The invention claimed is:

1. Whey protein-containing granules, comprising a polyglycerin fatty acid ester having HLB of 13 to 18 and containing lauric acid as its constituent fatty acid.

2. The whey protein-containing granules according to claim 1, wherein they contain 0.5 to 3% by weight of the polyglycerin fatty acid ester.

3. The whey protein-containing granules according to claim 1, wherein the polyglycerin fatty acid ester is a compound represented by the following formula (I):

[Formula 1]

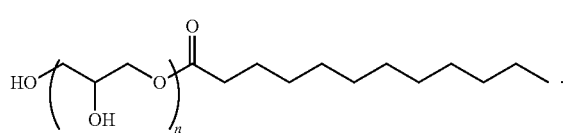

wherein n represents an integer of 1 to 15.

4. The whey protein-containing granules according to claim 1, wherein the polyglycerin fatty acid ester is a monolauric acid decaglycerin ester or monolauric acid pentaglycerin ester.

5. A method for producing whey protein-containing granules, comprising a step of granulating a whey protein with a polyglycerin fatty acid ester having HLB of 13 to 18 and containing lauric acid as its constituent fatty acid, optionally together with a binder.

6. A method for producing whey protein-containing granules, comprising steps of granulating a whey protein, optionally together with a binder, to obtain granules, and adding a polyglycerin fatty acid ester having HLB of 13 to 18 and containing lauric acid as its constituent fatty acid to the granules.

7. The method for producing the whey protein-containing granules according to claim 6, wherein the polyglycerin fatty acid ester is added by spraying the polyglycerin fatty acid ester to the granules.

8. The method for producing the whey protein-containing granules according to claim 5, wherein the polyglycerin fatty acid ester is a compound represented by the formula (I)

[Formula 1]

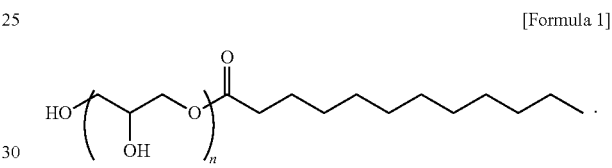

9. The method for producing the whey protein-containing granules according to claim 5, wherein the polyglycerin fatty acid ester is a monolauric acid decaglycerin ester or monolauric acid pentaglycerin ester.

10. A composition concurrently comprising the whey protein-containing granules according to claim 1 and a carrier.

11. A food comprising the whey protein-containing granules according to claim 1.

12. A drug comprising the whey protein-containing granules according to claim 1.

13. The method for producing the whey protein-containing granules according to claim 6, wherein the polyglycerin fatty acid ester is a compound represented by the formula (I)

[Formula 1]

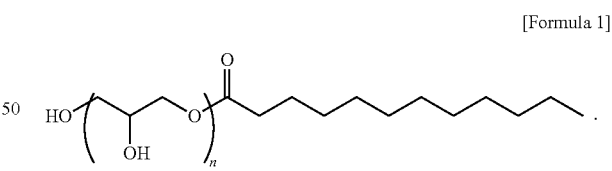

14. The method for producing the whey protein-containing granules according to claim 7, wherein the polyglycerin fatty acid ester is a compound represented by the formula (I)

[Formula 1]

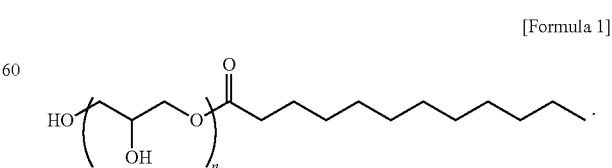

15. The method for producing the whey protein-containing granules according to claim 6, wherein the polyglycerin fatty acid ester is a monolauric acid decaglycerin ester or monolauric acid pentaglycerin ester.

16. The method for producing the whey protein-containing granules according to claim 7, wherein the polyglycerin fatty acid ester is a monolauric acid decaglycerin ester or monolauric acid pentaglycerin ester.

17. Whey protein-containing granules, comprising a polyglycerin fatty acid ester having HLB of 13 to 18 and containing lauric acid as its constituent fatty acid and binder.

18. Whey protein-containing granules according to claim 17, wherein the binder is pullulan, gum arabic, guar gum, xanthan gum or locust bean gum.

19. A method for producing whey protein-containing granules, comprising steps of granulating a whey protein together with a binder to obtain granules, and adding a polyglycerin fatty acid ester having HLB of 13 to 18 and containing lauric acid as its constituent fatty acid to the granules.

20. The method for producing whey protein-containing granules according to claim 19, wherein the binder is pullulan, gum arabic, guar gum, xanthan gum or locust bean gum.

* * * * *